(12) United States Patent
Kowaleski

(10) Patent No.: US 8,119,559 B2
(45) Date of Patent: *Feb. 21, 2012

(54) CATALYST, ITS PREPARATION AND USE

(75) Inventor: Ruth Mary Kowaleski, Cypress, TX (US)

(73) Assignee: BASF Corporation, Florham Park, NJ (US)

( * ) Notice: Subject to any disclaimer, the term of this patent is extended or adjusted under 35 U.S.C. 154(b) by 588 days.

This patent is subject to a terminal disclaimer.

(21) Appl. No.: 12/113,862

(22) Filed: May 1, 2008

(65) Prior Publication Data

US 2009/0062588 A1 Mar. 5, 2009

Related U.S. Application Data

(60) Provisional application No. 60/915,853, filed on May 3, 2007.

(51) Int. Cl.
*B01J 23/00* (2006.01)
*B01J 23/10* (2006.01)
*B01J 23/58* (2006.01)
*B01J 23/70* (2006.01)
*B01J 23/74* (2006.01)
*B01J 23/02* (2006.01)
*B01J 23/06* (2006.01)
*B01J 23/04* (2006.01)
*B01J 23/48* (2006.01)
*B01J 23/50* (2006.01)

(52) U.S. Cl. ........ 502/304; 502/306; 502/316; 502/317; 502/321; 502/328; 502/330; 502/338; 502/340; 502/344; 502/347

(58) Field of Classification Search .......... 502/302–306, 502/313, 321, 325, 326, 328, 330, 316–318, 502/331, 344–345, 338–340, 347
See application file for complete search history.

(56) References Cited

U.S. PATENT DOCUMENTS

| | | | | |
|---|---|---|---|---|
| 2,442,131 A | | 5/1948 | Kearby | 252/231.5 |
| 3,243,387 A | * | 3/1966 | Blume et al. | 502/330 |
| 3,872,027 A | | 3/1975 | Christmann et al. | 252/430 |
| 3,907,916 A | | 9/1975 | Soderquist et al. | 260/669 R |
| 4,005,049 A | * | 1/1977 | Fields | 502/330 |
| 4,607,055 A | * | 8/1986 | Grazioso et al. | 518/713 |
| 4,711,930 A | * | 12/1987 | Hoelderich et al. | 502/209 |
| 5,023,225 A | | 6/1991 | Williams et al. | 502/304 |
| 5,132,269 A | * | 7/1992 | Sasaki et al. | 502/205 |
| 5,380,967 A | * | 1/1995 | Steen et al. | 200/331 |
| 5,668,075 A | | 9/1997 | Milam et al. | 502/306 |
| 5,840,648 A | | 11/1998 | Suresh et al. | 502/306 |
| 5,962,757 A | * | 10/1999 | Milam et al. | 585/444 |
| 6,136,998 A | * | 10/2000 | Sasaki et al. | 558/322 |
| 6,417,136 B2 | * | 7/2002 | Cheung et al. | 502/330 |
| 6,551,958 B1 | * | 4/2003 | Baier et al. | 502/304 |
| 6,620,973 B2 | * | 9/2003 | Karim et al. | 568/478 |
| 7,067,562 B2 | * | 6/2006 | Espinoza et al. | 518/721 |
| 2003/0144566 A1 | * | 7/2003 | Culp et al. | 585/444 |
| 2004/0122115 A1 | | 6/2004 | Espinoza et al. | 518/721 |
| 2006/0009668 A1 | | 1/2006 | Wambaugh | 585/444 |

FOREIGN PATENT DOCUMENTS

| | | |
|---|---|---|
| CA | 2298227 | 8/2000 |
| CN | 1270851 | 10/2000 |
| CN | 101181687 | 5/2008 |
| DE | 19905392 | 8/2000 |
| EP | 1027928 | 2/2000 |
| EP | 1308442 | 11/2002 |
| WO | WO 03064032 | 8/2003 |
| WO | WO 2006055651 | 5/2006 |
| WO | WO 2007009927 | 1/2007 |

OTHER PUBLICATIONS

Hardeman R W et al., "Silver Substituted Lithium Iron Oxides," *Solid State Ionics*, North Holland Pub. Company, Amsterdam, NL, vol. 5, Oct. 1, 1981, pp. 347-349, XP025810550.

Liao S J et al., "Effect of $TiO_2$ on the Structure and Catalytic Behavior of Iron-Potassium Oxide Catalyst for Dehydrogenation of Ethylbenzene to Styrene," *Catalysis Communications*, Elsevier Science, Amsterdam, NL, vol. 9, May 15, 2008, pp. 1817-1821, XP022625412.

* cited by examiner

*Primary Examiner* — Steven Bos
*Assistant Examiner* — Anthony J Zimmer
(74) *Attorney, Agent, or Firm* — Raymond F. Keller

(57) ABSTRACT

A dehydrogenation catalyst is described comprising an iron oxide, an alkali metal or compound thereof, and silver or a compound thereof. Further a process is described for preparing a dehydrogenation catalyst that comprises preparing a mixture of iron oxide, an alkali metal or compound thereof, and silver or a compound thereof and calcining the mixture. A process for dehydrogenating a dehydrogenatable hydrocarbon and a process for polymerizing the dehydrogenated hydrocarbon are also described.

14 Claims, No Drawings

CATALYST, ITS PREPARATION AND USE

CROSS REFERENCE TO RELATED APPLICATION

This application claims priority to U.S. Provisional Application Ser. No. 60/915,853 filed May 3, 2007, the entire disclosure of which is herein incorporated by reference.

FIELD OF THE INVENTION

The present invention relates to a catalyst, a process for preparing the catalyst, and a process for the dehydrogenation of a dehydrogenatable hydrocarbon.

BACKGROUND

Dehydrogenation catalysts and the preparation of such catalysts are known in the art. Iron oxide based catalysts are customarily used in the dehydrogenation of dehydrogenatable hydrocarbons to yield, among other compounds, a corresponding dehydrogenated hydrocarbon. In this field of catalytic dehydrogenation of dehydrogenatable hydrocarbons to dehydrogenated hydrocarbons there are ongoing efforts to develop dehydrogenation catalysts that exhibit improved performance.

EP 1027928 discloses dehydrogenation catalysts based upon an iron oxide made by spray roasting an iron salt solution, and adding additional catalyst components selected from the group consisting of Be, Mg, Ca, Sr, Ba, Sc, Ti, Zr, Hf, V, Ta, Mo, W, Mn, Tc, Re, Ru, Os, Co, Rh, Ir, Ni, Pd, Pt, Cu, Ag, Au, Zn, Cd, Hg, Al, Ga, In, Tl, Na, Cs, La, Li, Ge, Sn, Pb, Bi, Ce, Pr, Nd, Pm, Sm, Eu, Gd, Tb, Dy, Ho, Er, Tm, Yb and Lu. These catalysts generally have one or more potassium compounds.

SUMMARY OF THE INVENTION

The present invention provides a dehydrogenation catalyst comprising an iron oxide, an alkali metal or compound thereof, and silver or a compound thereof.

In a preferred embodiment, the invention provides a dehydrogenation catalyst comprising an iron oxide, an alkali metal or compound thereof, and silver or a compound thereof wherein the silver or compound thereof is present in an amount of at least about 0.01 millimoles of silver per mole of iron oxide, calculated as $Fe_2O_3$.

In another preferred embodiment, the invention provides a dehydrogenation catalyst comprising iron oxide, an alkali metal or compound thereof, silver and silver ferrite.

In another preferred embodiment, the invention provides a dehydrogenation catalyst comprising iron oxide, potassium or a compound thereof, cerium or a compound thereof, calcium or a compound thereof, molybdenum or a compound thereof and silver.

The present invention further provides a process for preparing a dehydrogenation catalyst comprising preparing a mixture comprising an iron oxide, an alkali metal or compound thereof, and silver or a compound thereof wherein the silver or compound thereof is present in an amount of at least about 0.01 millimoles of silver per mole of iron oxide calculated as $Fe_2O_3$ and calcining the mixture.

The present invention provides a process for preparing a dehydrogenation catalyst comprising preparing a mixture of iron oxide, potassium or a compound thereof, cerium or a compound thereof, calcium or a compound thereof, molybdenum or a compound thereof and silver and calcining the mixture.

The present invention also provides a process for dehydrogenating a dehydrogenatable hydrocarbon comprising contacting a feed comprising a dehydrogenatable hydrocarbon with a catalyst comprising an iron oxide, an alkali metal or compound thereof, and silver or a compound thereof wherein the silver is present in an amount of at least about 0.01 millimoles of silver per mole of iron oxide, calculated as $Fe_2O_3$.

The present invention further provides a process for dehydrogenating a dehydrogenatable hydrocarbon comprising contacting a feed comprising a dehydrogenatable hydrocarbon with a catalyst comprising iron oxide, potassium or a compound thereof, cerium or a compound thereof, calcium or a compound thereof, molybdenum or a compound thereof and silver.

The present invention still further provides a method of using a dehydrogenated hydrocarbon for making polymers or copolymers, comprising polymerizing the dehydrogenated hydrocarbon to form a polymer or copolymer comprising monomer units derived from the dehydrogenated hydrocarbon, wherein the dehydrogenated hydrocarbon has been prepared in a process for the dehydrogenation of a dehydrogenatable hydrocarbon as described above.

DETAILED DESCRIPTION OF THE INVENTION

The present invention provides a catalyst that satisfies the need for improved dehydrogenation catalysts. The catalyst comprises an iron oxide, an alkali metal or compound thereof, and silver or a compound thereof. The catalyst comprising silver is more active and/or more selective than a similar catalyst that does not contain silver. Additionally, using this catalyst in the dehydrogenation of ethylbenzene to styrene may result in a reduced amount of α-methyl styrene in the product stream.

The dehydrogenation catalyst is an iron oxide based catalyst. In addition, the iron may be present in the form of potassium ferrite or as a compound with any of the other catalyst components including silver. The catalyst comprises from 10 to 90 wt % iron oxide, calculated as $Fe_2O_3$. The catalyst preferably comprises from 40 to 85 wt % iron oxide, and more preferably comprises from 60 to 80 wt % iron oxide.

The iron oxide may be formed or processed by any process known to those skilled in the art. Additionally, the catalyst may comprise one or more types of iron oxide. The iron oxide may be formed by heat decomposition of iron halide to form iron oxide as described in U.S. Patent Application Publication 2003/0144566, which is hereinafter referred to as regenerator iron oxide. The regenerator iron oxide may optionally be treated to reduce the residual halide content in the iron oxide to at most 2000 ppm or preferably at most 1500 ppm. The iron oxide may be formed by spray roasting of iron chloride in the presence of Group 6 metals or hydrolyzable metal chlorides. In the alternative, the iron oxide may be formed by a precipitation process. The iron oxide may be restructured by heating in the presence of a restructuring agent before its use in the catalyst by the process described in U.S. Pat. No. 5,668,075 and U.S. Pat. No. 5,962,757. The iron oxide may be treated, washed or heat conditioned before its use in this catalyst as described in U.S. Pat. No. 5,401,485. The iron oxide may be red, yellow, or black iron oxide. Yellow iron oxide is a hydrated iron oxide typically depicted as $Fe_2O_3H_2O$ or α-FeOOH. When yellow iron oxide is added, at least 5 wt %, or preferably at least 10 wt % of the total iron oxide in the catalyst, calculated as $Fe_2O_3$, may be yellow iron oxide, and at most 50 wt % of the total iron oxide may be yellow iron oxide. An example of a red iron oxide can be made by calcination of a yellow iron oxide made by the Penniman method. Iron oxide-providing compounds that may be present in the catalyst include goethite, hematite, magnetite, maghemite, and lepidocricite.

The catalyst also comprises an alkali metal selected from the group of alkali metals including lithium, sodium, potassium, rubidium, cesium and francium, and is preferably potassium. One or more of these metals may be used. The alkali metal may be present in the catalyst as a compound of an alkali metal. The alkali metals are generally present in a total quantity of at least 0.2 moles, preferably at least 0.25 moles, more preferably at least 0.45 moles, and most preferably at least 0.55 moles, per mole of iron oxide, calculated as $Fe_2O_3$. The alkali metals are generally present in a quantity of at most 5 moles, or preferably at most 1 mole, per mole of iron oxide. The alkali metal compound may include hydroxides; carbonates; bicarbonates; carboxylates, for example, formates, acetates, oxalates and citrates; nitrates; and oxides. The preferred alkali metal compound is potassium carbonate.

The catalyst also comprises silver that may be present as any compound of silver, for example silver oxide and silver ferrite or it may be present as silver metal. The silver may be added as silver ferrite, silver carbonate, silver nitrate, silver oxide, silver chromate, silver oxalate, silver powder, silver nanoparticles, or silver metal. In addition, silver compounds may convert to silver ferrite or other silver compounds during catalyst formation. The silver is generally present in a total quantity of at least 0.5 millimoles, preferably at least 1 millimole and more preferably at least 2.5 millimoles, and most preferably at least 10 millimoles per mole of iron oxide calculated as $Fe_2O_3$. The silver is generally present in a total quantity of at most 1 mole, and preferably at most 0.5 moles per mole of iron oxide.

The catalyst may further comprise a lanthanide. The lanthanide is selected from the group of lanthanides of atomic number in the range of from 57 to 66 inclusive. The lanthanide is preferably cerium. The lanthanide may be present as a compound of a lanthanide. The lanthanide is generally present in a total quantity of at least 0.02 moles, preferably at least 0.05 moles, more preferably at least 0.06 moles per mole of iron oxide, calculated as $Fe_2O_3$. The lanthanide is generally present in a total quantity of at most 0.2 moles, preferably at most 0.15 moles, more preferably at most 0.14 moles per mole of iron oxide. The lanthanide compound may include hydroxides; carbonates; bicarbonates; carboxylates, for example, formates, acetates, oxalates and citrates; nitrates; and oxides. The preferred lanthanide compound is cerium carbonate.

The catalyst may further comprise an alkaline earth metal or compound thereof. The alkaline earth metal may be calcium or magnesium, and it is preferably calcium. The alkaline earth metal compound is generally present in a quantity of at least 0.01 moles, and preferably at least 0.02 moles per mole of iron oxide calculated as $Fe_2O_3$. The alkaline earth metal compound is generally present in a quantity of at most 1 mole, and preferably at most 0.2 moles per mole of iron oxide.

The catalyst may further comprise a Group 6 metal or compound thereof. The Group 6 metal may be molybdenum or tungsten, and it is preferably molybdenum. The Group 6 metal is generally present in a quantity of at least 0.01 moles, preferably at least 0.02 moles per mole of iron oxide, calculated as $Fe_2O_3$. The Group 6 metal is generally present in a quantity of at most 0.5 moles, preferably at most 0.1 moles per mole of iron oxide.

Additional catalyst components that may be combined with the iron oxide include metals and compounds thereof selected from the group consisting of: Sc, Y, Ti, Zr, Hf, V, Nb, Ta, Cr, Mn, Tc, Re, Ru, Os, Co, Rh, Ir, Ni, Pd, Pt, Cu, Au, Zn, Cd, Hg, Al, Ga, In, Ti, Si, Ge, Sn, Pb, P, As, Sb, Bi, S, Se and Te. These components may be added by any method known to those skilled in the art. The additional catalyst components may include hydroxides; bicarbonates; carbonates; carboxylates, for example formates, acetates, oxalates and citrates; nitrates; and oxides. Palladium, platinum, ruthenium, rhodium, iridium, copper, and chromium are preferred additional catalyst components.

The catalyst may be prepared by any method known to those skilled in the art. For example, a paste may be formed comprising iron oxide, alkali metal or a compound thereof, silver or a compound thereof and any additional catalyst component(s). A mixture of these catalyst components may be mulled and/or kneaded or a homogenous or heterogeneous solution of any of these components may be impregnated on the iron oxide. Sufficient quantities of each component may be calculated from the composition of the catalyst to be prepared. Examples of applicable methods can be found in U.S. Pat. No. 5,668,075; U.S. Pat. No. 5,962,757; U.S. Pat. No. 5,689,023; U.S. Pat. No. 5,171,914; U.S. Pat. No. 5,190,906, U.S. Pat. No. 6,191,065, and EP 1027928, which are herein incorporated by reference.

In forming the catalyst, a mixture comprising iron oxide, alkali metal or a compound thereof, silver or a compound thereof and any additional catalyst component(s) may be shaped into pellets of any suitable form, for example, tablets, spheres, pills, saddles, trilobes, twisted trilobes, tetralobes, rings, stars, hollow and solid cylinders, and asymmetrically lobed particles as described in U.S. Patent Application Publication 2005/0232853. The addition of a suitable quantity of water, for example up to 30 wt %, typically from 2 to 20 wt %, calculated on the weight of the mixture, may facilitate the shaping into pellets. If water is added, it may be at least partly removed prior to calcination. Suitable shaping methods are pelletizing, extrusion, and pressing. Instead of pelletizing, extrusion or pressing, the mixture may be sprayed or spray dried to form a catalyst. If desired, spray drying may be extended to include pelletization and calcination.

An additional compound may be combined with the mixture that acts as an aid to the process of shaping and/or extruding the catalyst, for example a saturated or unsaturated fatty acid (such as palmitic acid, stearic acid, or oleic acid) or a salt thereof, a polysaccharide derived acid or a salt thereof, or graphite, starch, or cellulose. Any salt of a fatty acid or polysaccharide derived acid may be applied, for example an ammonium salt or a salt of any metal mentioned hereinbefore. The fatty acid may comprise in its molecular structure from 6 to 30 carbon atoms (inclusive), preferably from 10 to 25 carbon atoms (inclusive). When a fatty acid or polysaccharide derived acid is used, it may combine with a metal salt applied in preparing the catalyst, to form a salt of the fatty acid or polysaccharide derived acid. A suitable quantity of the additional compound is, for example, up to 1 wt %, in particular 0.001 to 0.5 wt %, relative to the weight of the mixture.

After formation, the catalyst mixture may be dried and calcined. Drying generally comprises heating the catalyst at a temperature of from about 30° C. to about 500° C., preferably from about 100° C. to about 300° C. Drying times are generally from about 2 minutes to 5 hours, preferably from about 5 minutes to about 1 hour. Calcination generally comprises heating the catalyst, typically in an inert, for example nitrogen or helium or an oxidizing atmosphere, for example an oxygen containing gas, air, oxygen enriched air or an oxygen/inert gas mixture. The calcination temperature is typically at least about 600° C., or preferably at least about 700° C., more preferably at least 825° C., and most preferably at least 880° C. The calcination temperature will typically be at most about 1600° C., or preferably at most about 1300° C. Typically, the duration of calcination is from 5 minutes to 12 hours, more typically from 10 minutes to 6 hours.

The catalyst formed according to the invention may exhibit a wide range of physical properties. The surface structure of the catalyst, typically in terms of pore volume, median pore diameter and surface area, may be chosen within wide limits. The surface structure of the catalyst may be influenced by the selection of the temperature and time of calcination, and by the application of an extrusion aid.

Suitably, the pore volume of the catalyst is at least 0.01 ml/g, more suitably at least 0.05 ml/g. Suitably, the pore volume of the catalyst is at most 0.5, preferably at most 0.4 ml/g, more preferably at most 0.3 ml/g, and most preferably at most 0.2 ml/g. Suitably, the median pore diameter of the catalyst is at least 500 Å, in particular at least 1000 Å. Suitably, the median pore diameter of the catalyst is at most 20000 Å, in particular at most 15000 Å. In a preferred embodiment, the median pore diameter is in the range of from 2000 to 10000 Å. As used herein, the pore volumes and median pore diameters are as measured by mercury intrusion according to ASTM D4282-92, to an absolute pressure of 6000 psia (4.2× $10^7$ Pa) using a Micromeretics Autopore 9420 model; (1300 contact angle, mercury with a surface tension of 0.473 N/m). As used herein, median pore diameter is defined as the pore diameter at which 50% of the mercury intrusion volume is reached.

The surface area of the catalyst is preferably in the range of from 0.01 to 20 m$^2$/g, more preferably from 0.1 to 10 m$^2$/g.

The crush strength of the catalyst is suitably at least 10 N/mm, and more suitably it is in the range of from 20 to 100 N/mm, for example about 55 or 60 N/mm.

In another aspect, the present invention provides a process for the dehydrogenation of a dehydrogenatable hydrocarbon by contacting a dehydrogenatable hydrocarbon and steam with an iron oxide based catalyst made according to the invention to produce the corresponding dehydrogenated hydrocarbon.

The dehydrogenated hydrocarbon formed by the dehydrogenation process is a compound having the general formula:

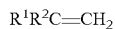

wherein R$^1$ and R$^2$ independently represent an alkyl, alkenyl or a phenyl group or a hydrogen atom.

The dehydrogenatable hydrocarbon is a compound having the general formula:

wherein R$^1$ and R$^2$ independently represent an alkyl, alkenyl or a phenyl group or a hydrogen atom.

A suitable phenyl group may have one or more methyl groups as substitutes. A suitable alkyl group generally has from 2 to 20 carbon atoms per molecule, and preferably from 3 to 8 carbon atoms such as in the case of n-butane and 2-methylbutane. Suitable alkyl substituents are propyl (—CH$_2$—CH$_2$—CH$_3$), 2-propyl (i.e., 1-methylethyl, —CH(—CH$_3$)$_2$), butyl (—CH$_2$—CH$_2$—CH$_2$—CH$_3$), 2-methylpropyl (—CH$_2$—CH(—CH$_3$)$_2$), and hexyl (—CH$_2$—CH$_2$—CH$_2$—CH$_2$—CH$_2$—CH$_3$), in particular ethyl (—CH$_2$—CH$_3$). A suitable alkenyl group generally has from about 4 to about 20 carbon atoms per molecule, and preferably from 4 to 8 carbon atoms per molecule.

The dehydrogenatable hydrocarbon may be an alkyl substituted benzene, although other aromatic compounds may be applied as well, such as alkyl substituted naphthalene, anthracene, or pyridine. Examples of suitable dehydrogenatable hydrocarbons are butyl-benzene, hexylbenzene, (2-methylpropyl)benzene, (1-methylethyl)benzene (i.e., cumene), 1-ethyl-2-methyl-benzene, 1,4-diethylbenzene, ethylbenzene, 1-butene, 2-methylbutane and 3-methyl-1-butene. It is possible to convert n-butane with the present process via 1-butene into 1,3-butadiene and 2-methylbutane via tertiary amylenes into isoprene.

Examples of dehydrogenated hydrocarbons that can be produced by the process are butadiene, alpha-methyl styrene, divinylbenzene, isoprene and styrene.

The dehydrogenation process is frequently a gas phase process; wherein a gaseous feed comprising the reactants is contacted with the solid catalyst. The catalyst may be present in the form of a fluidized bed of catalyst particles or in the form of a packed bed. The process may be carried out as a batch process or as a continuous process. Hydrogen may be a further product of the dehydrogenation process, and the dehydrogenation in question may be a non-oxidative dehydrogenation. Examples of applicable methods for carrying out the dehydrogenation process can be found in U.S. Pat. No. 5,689,023; U.S. Pat. No. 5,171,914; U.S. Pat. No. 5,190,906; U.S. Pat. No. 6,191,065, and EP 1027928, which are herein incorporated by reference.

It is advantageous to apply water, which may be in the form of steam, as an additional component of the feed. The presence of water will decrease the rate of deposition of coke on the catalyst during the dehydrogenation process. Typically the molar ratio of water to the dehydrogenatable hydrocarbon in the feed is in the range of from 1 to 50, more typically from 3 to 30, for example from 5 to 10.

The dehydrogenation process is typically carried out at a temperature in the range of from 500 to 700° C., more typically from 550 to 650° C., for example 600° C., or 630° C. In one embodiment, the dehydrogenation process is carried out isothermally. In other embodiments, the dehydrogenation process is carried out in an adiabatic manner, in which case the temperatures mentioned are reactor inlet temperatures, and as the dehydrogenation progresses the temperature may decrease typically by up to 150° C., more typically by from 10 to 120° C. The absolute pressure is typically in the range of from 10 to 300 kPa, more typically from 20 to 200 kPa, for example 50 kPa, or 120 kPa.

If desired, one, two, or more reactors, for example three or four, may be applied. The reactors may be operated in series or parallel. They may or may not be operated independently from each other, and each reactor may be operated under the same conditions or under different conditions.

When operating the dehydrogenation process as a gas phase process using a packed bed reactor, the LHSV may preferably be in the range of from 0.01 to 10 h$^{-1}$, more preferably in the range of from 0.1 to 2 h$^{-1}$. As used herein, the term "LHSV" means the Liquid Hourly Space Velocity, which is defined as the liquid volumetric flow rate of the hydrocarbon feed, measured at normal conditions (i.e., 0° C. and 1 bar absolute), divided by the volume of the catalyst bed, or by the total volume of the catalyst beds if there are two or more catalyst beds.

The conditions of the dehydrogenation process may be selected such that the conversion of the dehydrogenatable hydrocarbon is in the range of from 20 to 100 mole %, preferably from 30 to 80 mole %, or more preferably from 35 to 75 mole %.

The activity (T70) of the catalyst is defined as the temperature under given operating conditions at which the conversion of the dehydrogenatable hydrocarbon in a dehydrogenation process is 70 mole %. A more active catalyst thus has a lower T70 than a less active catalyst. The corresponding selectivity (S70) is defined as the selectivity to the desired product at the temperature at which conversion is 70 mole %.

The dehydrogenated hydrocarbon may be recovered from the product of the dehydrogenation process by any known means. For example, the dehydrogenation process may include fractional distillation or reactive distillation. If desirable, the dehydrogenation process may include a hydrogenation step in which at least a portion of the product is subjected to hydrogenation by which at least a portion of any byproducts formed during dehydrogenation, are converted into the dehydrogenated hydrocarbon. The portion of the product subjected to hydrogenation may be a portion of the product that is enriched in the byproducts. Such hydrogenation is known in the art. For example, the methods known from U.S. Pat. No. 5,504,268; U.S. Pat. No. 5,156,816; and U.S. Pat. No. 4,822,936, which are incorporated herein by reference, are readily applicable to the present invention.

One preferred embodiment of a dehydrogenation process is the nonoxidative dehydrogenation of ethylbenzene to form styrene. This embodiment generally comprises feeding a feed comprising ethylbenzene and steam to a reaction zone containing catalyst at a temperature of from about 500° C. to about 700° C. Steam is generally present in the feed at a steam to hydrocarbon molar ratio of from about 7 to about 15. In the alternative this process may be carried out at a lower steam to hydrocarbon molar ratio of from about 1 to about 7, preferably of from about 2 to about 6. This process typically produces small amounts of byproducts, for example phenylacetylene and alpha-methyl styrene, in addition to styrene. Alpha-methyl styrene is an undesired byproduct because it acts as a chain terminator when the styrene is later polymerized.

Another preferred embodiment of a dehydrogenation process is the oxidative dehydrogenation of ethylbenzene to form styrene. This embodiment generally comprises feeding ethylbenzene and an oxidant, for example, oxygen, iodide, sulfur, sulfur dioxide, or carbon dioxide to a reaction zone containing catalyst at a temperature of from about 500° C. to about 800° C. The oxidative dehydrogenation reaction is exothermic so the reaction can be carried out at lower temperatures and/or lower steam to oil ratios.

Another preferred embodiment of a dehydrogenation process is the dehydrogenation of isoamylenes to form isoprene. This embodiment generally comprises feeding a mixed isoamylene feed comprising 2-methyl-1-butene, 2-methyl-2-butene, and 3-methyl-1-butene into a reaction zone containing catalyst at a temperature of from about 525° C. to about 675° C. The process is typically conducted at atmospheric pressure. Steam is generally added to the feed at a steam to hydrocarbon molar ratio of from about 13.5 to about 31.

Another preferred embodiment of a dehydrogenation process is the dehydrogenation of butene to form butadiene. This embodiment generally comprises feeding a mixed butylenes feed comprising 1-butene and 2-butene (cis and/or trans isomers) to a reaction zone containing catalyst at a temperature of from about 500° C. to about 700° C.

Due to the endothermic nature of most of these dehydrogenation processes, additional heat input is often desirable to maintain the required temperatures to maintain conversion and selectivity. The heat can be added before a reaction zone, between reaction zones when there are two or more zones, or directly to the reaction zone.

A preferred embodiment of a suitable heating method is the use of a conventional heat exchanger. The process stream may be heated before entering the first or any subsequent reactors. Preferred sources of heat include steam and other heated process streams.

Another preferred embodiment of a suitable heating method is the use of a flameless distributed combustion heater system as described in U.S. Pat. No. 7,025,940, which is herein incorporated by reference.

Another preferred embodiment of a suitable heating method is catalytic or noncatalytic oxidative reheat. Embodiments of this type of heating method are described in U.S. Pat. No. 4,914,249; U.S. Pat. No. 4,812,597; and U.S. Pat. No. 4,717,779; which are herein incorporated by reference.

The dehydrogenated hydrocarbon produced by the dehydrogenation process may be used as a monomer in polymerization processes and copolymerization processes. For example, the styrene obtained may be used in the production of polystyrene and styrene/diene rubbers. The improved catalyst performance achieved by this invention with a lower cost catalyst leads to a more attractive process for the production of the dehydrogenated hydrocarbon and consequently to a more attractive process which comprises producing the dehydrogenated hydrocarbon and the subsequent use of the dehydrogenated hydrocarbon in the manufacture of polymers and copolymers which comprise monomer units of the dehydrogenated hydrocarbon. For applicable polymerization catalysts, polymerization processes, polymer processing methods and uses of the resulting polymers, reference is made to H. F. Marks, et al. (ed.), "Encyclopedia of Polymer Science and Engineering", $2^{nd}$ Edition, new York, Volume 16, pp 1-246, and the references cited therein.

The following examples are presented to illustrate the invention, but they should not be construed as limiting the scope of the invention.

Example 1 (Comparative)

A catalyst was prepared by combining: 900 g iron oxide ($Fe_2O_3$) (made by heat decomposition of iron chloride) that contained 0.08 wt % Cl and had a surface area of 3.2 $m^2$/g and 100 g yellow iron oxide (FeOOH) with sufficient potassium carbonate, cerium carbonate (as hydrated $Ce_2(CO_3)_3$ containing 52 wt % Ce), molybdenum trioxide, and calcium carbonate to give a catalyst with 18 mmoles Mo per mole of iron oxide and the other components as shown in Table 1. Water (about 10 wt %, relative to the weight of the dry mixture) was added to form a paste, and the paste was extruded to form 3 mm diameter cylinders that were then cut into 6 mm lengths. The pellets were dried in air at 170° C. for 15 minutes and subsequently calcined in air at 888° C. for 1 hour. The composition of the catalyst after calcination is shown in Table 1 as millimoles per mole of iron oxide, calculated as $Fe_2O_3$.

A 100 $cm^3$ sample of the catalyst was used for the preparation of styrene from ethylbenzene under isothermal testing conditions in a reactor designed for continuous operation. The conditions were as follows: absolute pressure 76 kPa, steam to ethylbenzene molar ratio 10, and LHSV 0.65 $h^{-1}$. In this test, the temperature was initially held at 595° C. for a period of about 5-10 days. The temperature was later adjusted such that a 70 mole % conversion of ethylbenzene was achieved (T70). The selectivity (S70) to styrene at the selected temperature was measured.

Examples 2-17

Catalysts were prepared according to the invention. The ingredients described in Example 1 were used. Some of the examples used different amounts of these ingredients as shown by the catalyst compositions in Table 1. Additionally the calcination temperatures are shown in Table 1 because some of the catalysts were calcined at different temperatures. The catalysts of examples 2-17 contained silver that was added in the form of silver oxide in different amounts. The catalysts were tested under the same conditions as the catalyst of Example 1, and the catalyst performance is shown in Table 1.

TABLE 1

| Example | Composition, millimoles/mole of iron oxide | | | | | Calc. T °C. | T70 °C. | S70 % |
|---|---|---|---|---|---|---|---|---|
| | Ag | Mo | Ce | Ca | K | | | |
| 1 (Comp) | 0 | 18 | 100 | 25 | 623 | 888 | 593.5 | 95.0 |
| 2 | 25.7 | 18 | 100 | 25 | 623 | 888 | 590.1 | 95.6 |
| 3 | 135 | 18 | 100 | 25 | 623 | 888 | 588.4 | 95.3 |
| 4 | 244.3 | 18 | 100 | 25 | 623 | 888 | 589.5 | 95.4 |
| 5 | 70 | 18 | 75 | 25 | 623 | 800 | 586.3 | 95.0 |
| 6 | 70 | 18 | 75 | 25 | 623 | 975 | 591.8 | 96.0 |
| 7 | 200 | 18 | 75 | 25 | 623 | 800 | 590.2 | 94.8 |
| 8 | 200 | 18 | 75 | 25 | 623 | 975 | 596.0 | 95.6 |
| 9 | 70 | 18 | 125 | 25 | 623 | 800 | 585.8 | 94.3 |
| 10 | 70 | 18 | 125 | 25 | 623 | 975 | 585.9 | 95.9 |
| 11 | 200 | 18 | 125 | 25 | 623 | 800 | 585.2 | 94.6 |
| 12 | 200 | 18 | 125 | 25 | 623 | 975 | 588.2 | 95.8 |
| 13 | 135 | 18 | 142 | 25 | 623 | 740 | 584.4 | 93.9 |
| 14 | 135 | 18 | 100 | 25 | 623 | 1035 | 588.5 | 96.2 |
| 15 | 135 | 18 | 100 | 75 | 623 | 888 | 590.3 | 95.9 |
| 16 | 135 | 18 | 100 | 25 | 675 | 888 | 586.8 | 95.5 |
| 17 | 135 | 18 | 100 | 25 | 575 | 888 | 589.5 | 95.3 |

As can be seen from Examples 1-4, a catalyst having the same ingredients and being calcined at the same temperature is more active and more selective if it contains silver. Examples 5-12 show the affects of changing the amount of cerium and the calcination temperature of the catalyst. Examples 13 and 14 show catalysts that were calcined at different temperatures, with the catalyst of Example 13 being calcined at 740° C., and the catalyst of Example 14 being calcined at 1035° C. Examples 15-17 demonstrate the effect on catalyst performance of changing the amount of calcium and potassium in the catalyst.

Examples 18 (Comparative) and 19

Examples 18-19 demonstrate the catalyst performance observed when the iron oxide used is not the same as that used in Examples 1-17. In Example 18, a catalyst was prepared using red iron oxide made by the heat treatment of a precipitated yellow iron oxide. The surface area of the red iron oxide was 5.1 m²/g and the red iron oxide contained less than 10 ppmw of chloride. The yellow iron oxide was made from oxidation of iron sulfate. The following ingredients were combined: 1000 g of the above described iron oxide, sufficient potassium carbonate, cerium carbonate (as hydrated $Ce_2(CO_3)_3$ containing 52 wt % Ce), molybdenum trioxide, and calcium carbonate to give the composition shown in Table 2. Water (about 10 wt %, relative to the weight of the dry mixture) was added to form a paste, and the paste was extruded to form 3 mm diameter cylinders that were then cut into 6 mm lengths. The pellets were dried in air at 170° C. for 15 minutes and subsequently calcined in air at 875° C. for 1 hour. The catalyst of Example 19 was prepared in the same manner as that of Example 18, except that silver oxide was added to give the composition shown in Table 2. The catalyst performance of the catalysts of Examples 18 and 19 were tested using the same method as in Examples 1-17, except the temperature was initially held at 600° C. The results are shown in Table 2.

Examples 20 (Comparative) and 21

Examples 20-21 demonstrate the catalyst performance observed when regenerator iron oxide made by heat decomposition is used as in Examples 1-17, but it is restructured before its use in the catalyst as described above. In Example 20, a mixture was prepared by calcining 1000 g of regenerator iron oxide with sufficient molybdenum trioxide at 995° C. to produce a restructured iron oxide composition comprising 19.5 millimole of molybdenum per mole of iron oxide, calculated as $Fe_2O_3$. The restructured iron oxide composition was combined with sufficient potassium carbonate, cerium carbonate (as hydrated $Ce_2(CO_3)_3$ containing 52 wt % Ce), and calcium carbonate to give the composition shown in Table 2. Water (about 5 wt %, relative to the weight of the dry mixture) was added to form a paste, and the paste was extruded to form 3 mm diameter cylinders that were then cut into 6 mm lengths. The pellets were dried in air at 170° C. for 15 minutes and subsequently calcined in air at 775° C. for 1 hour. The composition of the catalyst after calcination is shown in Table 2. The catalyst of Example 21 was prepared in the same manner as that of Example 20, except that silver oxide was added along with the potassium, cerium and calcium carbonates to give the composition shown in Table 2. The catalysts of Examples 20 and 21 were tested using the same method as in Examples 1-17, except the temperature was initially held at 600° C. The results are shown in Table 2.

TABLE 2

| Example | Composition, millimoles/mole of iron oxide | | | | | Calc. T °C. | T70 °C. | S70 % |
|---|---|---|---|---|---|---|---|---|
| | Ag | Mo | Ce | Ca | K | | | |
| 18 (Comp) | 0 | 11 | 89 | 67 | 623 | 875 | 588.9 | 94.6 |
| 19 | 70 | 11 | 89 | 67 | 623 | 875 | 590.5 | 95.3 |
| 20 (Comp) | 0 | 19.5 | 96 | 25 | 612 | 775 | 594.6 | 95.3 |
| 21 | 70 | 19.5 | 96 | 25 | 612 | 775 | 587.9 | 95.6 |

As can be seen from Examples 18-19, a non-regenerator iron oxide based catalyst that has silver is more selective than a similar catalyst that does not have silver. As can be seen from Examples 20-21, a restructured iron oxide based catalyst that has silver is more active and more selective than a similar catalyst that does not have silver.

Examples 22 (Comparative) and 23-27

Catalysts were prepared according to the process of Examples 1-17. The ingredients were used in different amounts and the catalyst composition after calcination is shown in Table 3. The catalysts of Examples 22-27 were tested according to the same method of the above examples. The amount of α-methyl styrene (AMS) in the product was measured and is shown in Table 3 as ppmw relative to the weight of the condensed product stream from the dehydrogenation reactor. The α-methyl styrene levels were tested by gas chromatograph at the T70 temperature. Example 22 depicts the average results for three catalysts with the same composition.

TABLE 3

| Example | Composition, millimoles/mole iron oxide | | | | | Calc T °C. | T70 °C. | S70 % | AMS ppmw |
|---|---|---|---|---|---|---|---|---|---|
| | Ag | Mo | Ce | Ca | K | | | | |
| 22 (Comp) | 0 | 18 | 122 | 25 | 623 | 950 | 595.9 | 95.5 | 260 |
| 23 | 70 | 18 | 125 | 25 | 623 | 975 | 588.1 | 95.8 | 226 |
| 24 | 70 | 18 | 125 | 25 | 623 | 1035 | 590.0 | 96.4 | 248 |
| 25 | 100 | 18 | 150 | 25 | 623 | 1035 | 592.8 | 95.8 | 218 |
| 26 | 150 | 18 | 150 | 25 | 623 | 1035 | 594.9 | 95.8 | 235 |
| 27 | 200 | 18 | 150 | 25 | 623 | 1035 | 588.7 | 96.2 | 225 |

As can be seen from Examples 22-27, an iron oxide based dehydrogenation catalyst containing silver can result in the production of a reduced amount of alpha-methyl styrene impurity in an ethylbenzene dehydrogenation process.

One skilled in the art can vary many of the variables shown above in addition to other variables to achieve a dehydrogenation catalyst that is most effective for a particular application. Additional catalyst components may also be added to affect the properties and performance of the catalyst. The catalyst manufacturing process may be altered with respect to such variables as drying times and temperatures, calcination times and temperatures, and processing speed to affect the properties and performance of the catalyst.

What is claimed is:

1. A dehydrogenation catalyst comprising iron oxide, potassium or a compound thereof, cerium or a compound thereof, calcium or a compound thereof, molybdenum or a compound thereof and silver.

2. A dehydrogenation catalyst comprising an iron oxide, an alkali metal or compound thereof, a Group 6 metal or compound thereof, and silver or a compound thereof wherein the silver or compound thereof is present in an amount of from about 0.01 millimoles to 500 millimoles of silver per mole of iron oxide, calculated as $Fe_2O_3$.

3. A catalyst as claimed in claim 2 wherein the silver or a compound thereof is present in an amount of from about 0.25 to about 500 millimoles of silver per mole of iron oxide, calculated as $Fe_2O_3$.

4. A catalyst as claimed in claim 2 wherein the silver or a compound thereof is present in an amount of from about 1 to about 300 millimoles of silver per mole of iron oxide, calculated as $Fe_2O_3$.

5. A catalyst as claimed in claim 2 wherein the silver or a compound thereof is present in an amount of from about 10 to about 100 millimoles of silver per mole of iron oxide, calculated as $Fe_2O_3$.

6. A catalyst as claimed in claim 2 wherein the alkali metal or compound thereof comprises potassium.

7. A catalyst as claimed in claim 2 wherein the catalyst further comprises a lanthanide or a compound thereof.

8. A catalyst as claimed in claim 7 wherein the lanthanide or compound thereof comprises cerium.

9. A catalyst as claimed in claim 2 further comprising an alkaline earth metal or compound thereof.

10. A catalyst as claimed in claim 9 wherein the alkaline earth metal or compound thereof comprises calcium.

11. A catalyst as claimed in claim 1 wherein the Group 6 metal or compound thereof comprises molybdenum.

12. A catalyst as claimed in claim 2 wherein the catalyst further comprises a metal selected from the group consisting of palladium, platinum, ruthenium, osmium, rhodium, iridium, titanium and copper.

13. A catalyst as claimed in claim 2 wherein the iron oxide comprises regenerator iron oxide formed by the heat decomposition of an iron halide.

14. A catalyst as claimed in claim 2 wherein the iron oxide is restructured by heat treating in the presence of a restructuring agent.

* * * * *